United States Patent [19]

Ament et al.

[11] Patent Number: 5,216,409

[45] Date of Patent: Jun. 1, 1993

[54] METHOD AND APPARATUS FOR DETECTING A CONTAMINATED ALCOHOL-GASOLINE FUEL MIXTURE

[75] Inventors: Frank Ament, Troy; Eugene V. Gonze, Sterling Heights, both of Mich.

[73] Assignee: General Motors Corporation, Detroit, Mich.

[21] Appl. No.: 752,344

[22] Filed: Sep. 3, 1991

[51] Int. Cl.$^5$ ............................................. B60Q 1/00
[52] U.S. Cl. ................................ 340/438; 340/450.2; 123/575; 73/307
[58] Field of Search ............... 340/450, 450.2, 603, 340/620, 438, 450.2; 123/575; 364/550, 431.02, 431.03; 73/304 R, 304 C, 307, 308

[56] References Cited

U.S. PATENT DOCUMENTS

| | | | |
|---|---|---|---|
| 4,316,174 | 2/1982 | Sutton et al. | 340/620 |
| 4,369,736 | 1/1983 | Ito | 123/575 |
| 4,629,334 | 12/1986 | Hochstein | 73/304 R |
| 4,638,305 | 1/1987 | Sutton | 73/304 C |
| 4,765,187 | 8/1988 | Weinstein | 73/304 R |
| 4,905,655 | 3/1990 | Maekawa | 123/575 |
| 4,915,084 | 4/1990 | Gonze | 123/575 |
| 5,033,293 | 7/1991 | Honma et al. | 73/118.1 |

OTHER PUBLICATIONS

"Intelligent Alcohol Fuel Sensor," G. Schmitz, R. Bartz, and U. Hilger SAE Paper No. 900231, 1990, pp. 1-7.

*Primary Examiner*—Jin F. Ng
*Assistant Examiner*—Edward Lefkowitz
*Attorney, Agent, or Firm*—Jimmy I. Funke

[57] ABSTRACT

A method and apparatus are described for detecting dissolved contaminants in an alcohol-gasoline mixture used for fueling an internal combustion engine and then indicating that the fuel mixture is of substandard quality when the degree of contamination reaches an unacceptable level. The resistivity of the fuel mixture, which varies as a function of the degree of contamination, is measured using a sensor positioned in the engine fuel supply line. When the measured resistivity of the fuel decreases below a threshold amount, an indication of substandard fuel quality is provided. The threshold amount may be a fixed constant, or its value may vary depending upon the proportion of alcohol to gasoline in the fuel mixture. The composition of the fuel mixture is determined by using a capacitive sensor to measuring the fuel dielectric constant. A separate resistive sensor may be used for sensing fuel resistivity, or the same sensor used for sensing the fuel dielectric constant can be switched between resistive and capacitive measuring circuitry.

1 Claim, 4 Drawing Sheets

METHOD AND APPARATUS FOR DETECTING A CONTAMINATED ALCOHOL-GASOLINE FUEL MIXTURE

BACKGROUND OF THE INVENTION

This invention relates to a method and apparatus for detecting contaminants dissolved in an alcohol-gasoline fuel mixture that is delivered to an internal combustion engine, and more particularly, to a method and apparatus for providing an indication of substandard fuel quality when the degree of contamination reaches an unacceptable level.

Alcohols such as ethanol or methanol have been proposed as possible alternatives to gasoline for fueling conventional internal combustion engines. Although it is possible to operate an engine on a pure alcohol fuel, gasoline is generally mixed with the alcohol to increase the fuel vapor pressure and improve engine starting and warm-up operation.

For an engine capable of operating on a variable alcohol-gasoline fuel mixture, it is necessary to know the relative concentrations of alcohol and gasoline in the fuel to effectively control the engine air-fuel ratio for optimal combustion. It is well known that the dielectric constant of such a fuel is related to the proportion of alcohol to gasoline in the mixture. In the prior art, this relationship has been utilized for determining the composition of variable alcohol-gasoline fuel mixtures. For example, U.S. Pat. No. 4,915,084 issued to E. V. Gonze on Apr. 10, 1990, which has been assigned to the assignee of the present application, discloses a capacitive sensor positioned in an engine fuel supply line and a capacitance measuring circuit for determining the fuel dielectric constant, and hence, the composition of the fuel mixture flowing through the sensor to the engine.

One problem associated with alcohol-gasoline fuel mixtures, that has not heretofore been addressed, is that of fuel contamination. Alcohol based fuels, especially those containing methanol, have the capacity to dissolve large quantities of water and other ionic contaminants due to the relatively large dipole moment associated with alcohols. In sufficient amounts, these dissolved fuel contaminants can cause the failure of components in the fuel supply system such as the fuel pump, fuel filter, fuel injectors, and the fuel composition sensor.

SUMMARY OF THE INVENTION

It is the general object of the present invention to provide a method and apparatus for detecting contaminants in an alcohol-gasoline fuel mixture delivered to an internal combustion engine and indicating that the fuel mixture is considered to be substandard in quality when the degree of contamination reaches an unacceptable level. This is accomplished by measuring the electrical resistivity of the alcohol-gasoline fuel mixture, which varies as a function of the quantity of dissolved contaminants in the fuel mixture; and providing an indication of substandard fuel quality when the measured resistivity of the fuel is less than a threshold amount.

It has been found that the resistivity of an alcohol-gasoline fuel mixture affords a good indication of the degree of contamination of the fuel mixture. The larger the degree of contamination, the lower will be the value of the measured fuel resistivity. As a result, a threshold amount can be selected to define the lower bound for acceptable fuel resistivity and the related level of acceptable contamination. A warning indication can then be provided if the fuel resistivity falls below the threshold amount, thereby alerting an operator that fuel of a substandard quality is being delivered to the engine. Once such a warning is provided, steps can be taken to eliminate the contaminated fuel and/or to avoid the source of poor quality fuel in the future. The warning indication also provides diagnostic information in the event of fuel system failure due to the delivery of substandard fuel, and with early warning the durability of fuel system components can be increased.

For carrying out the invention, a sensor means is positioned in the a fuel supply line that delivers the alcohol-gasoline mixture to the engine. The sensor means is adapted for fuel to flow therethrough, and is capable of measuring at least one electrical property of the alcohol-gasoline mixture, such as the resistivity and/or the dielectric constant. Resistance measuring circuitry is coupled to the sensor means for developing a resistance signal indicative of the fuel resistivity. Means responsive to the resistance signal is then employed to provide an indication of substandard fuel quality when the measured fuel resistivity is less than a threshold amount.

For a given degree of contamination, it has been found that fuel resistivity increases with decreasing alcohol content in the fuel mixture. Consequently, fuels having smaller concentrations of alcohol can have resistivities greater than a fixed threshold amount, even though they are severely contaminated and are considered substandard in quality.

In a further embodiment of the invention, capacitance measuring circuitry is also coupled to the sensor means for measuring the dielectric constant of the alcohol-gasoline fuel mixture and for developing a capacitance signal indicative of the fuel dielectric constant. The fuel dielectric constant is known to vary in accordance with the relative proportion of alcohol to gasoline in the fuel mixture. Additional means responsive to this capacitance signal is then provided for selecting a threshold amount based upon the composition of the alcohol-gasoline fuel mixture as indicated by the measured dielectric constant. Thus, by providing a variable threshold amount having a value determined by the composition of the fuel mixture, the determination of substandard fuel quality can be made independent of the concentration of alcohol in the fuel mixture.

In yet another embodiment of the invention, a switching means is provided for selectively switching the sensor means between the resistance measuring circuitry and the capacitance measuring circuitry in accordance with predetermined switching criteria. Without this switching means, the sensor means requires a separate resistance sensor for sensing fuel resistivity and a separate capacitance sensor for sensing the fuel dielectric constant. With the switching means, a single sensor capable of sensing both fuel resistivity and dielectric constant can be alternately switched between the resistance and capacitance measuring means. This reduces the expense and complexity of the sensing means, since a single sensor can be employed to perform both resistance and capacitance sensing functions. In addition, it has been found that the corrosive effect of the fuel on the sensor electrodes is diminished, since the period of time that direct current is applied to the electrodes when measuring fuel resistivity is reduced by the switching.

These and other aspects and advantages of the invention may be best understood by reference to the following detailed description of the preferred embodiments when considered in conjunction with the accompanying drawings.

DESCRIPTION OF THE PREFERRED EMBODIMENTS

In the description that follows, similar parts or structures used in the figures will be designated with like numerals, and where such parts and structures have been previously discussed with respect to an earlier figure, the description will not be repeated.

Figure 1:
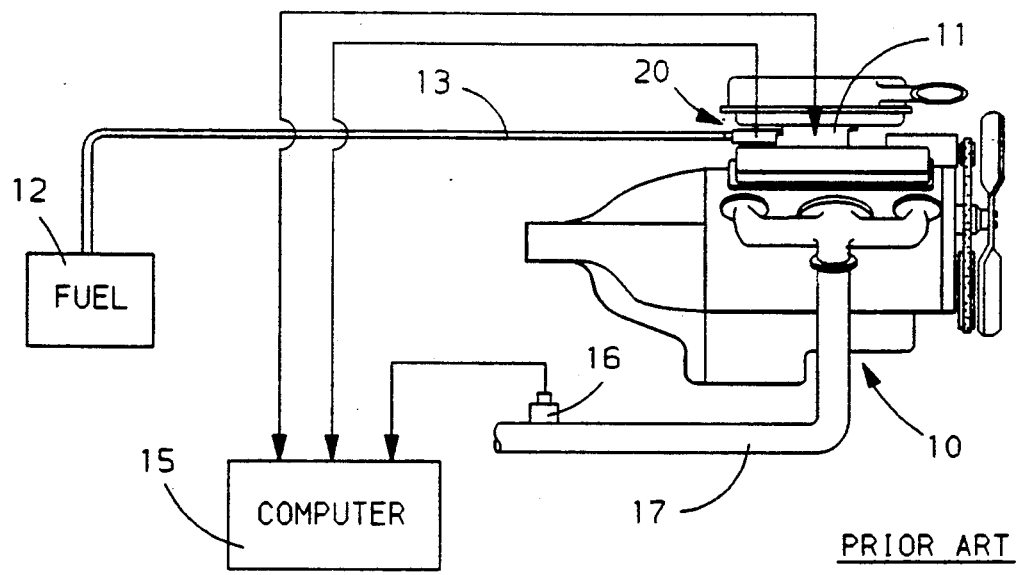
FIG. 1 illustrates an internal combustion engine including a fuel supply system for delivering an alcohol-gasoline fuel mixture to the engine and a prior art system for controlling the engine air-fuel ratio based on the sensed dielectric constant of the fuel mixture.

Referring now to FIG. 1, there is shown a prior art system for controlling the air-fuel ratio of an internal combustion engine 10 that is fueled with an alcohol-gasoline fuel mixture. The engine 10 has a fuel supply system including a fuel tank 12, a fuel supply line 13, a fuel composition sensor 20, and an air/fuel induction apparatus 11, such as a carburetor or fuel injection system. The fuel system includes other standard components such as a fuel pump and fuel filter, which have not been specifically shown in FIG. 1.

As the engine 10 is operated, a fuel mixture containing alcohol and gasoline in an unknown ratio is pumped from fuel tank 12 through the fuel supply line 13 to the fuel composition sensor 20, and then to the air/fuel induction apparatus 11. The proportion of air to fuel or the air-fuel ratio of the fuel mixture provided by apparatus 11 is controlled in response to a signal from computer 15, which may be a programmed digital computer of the type used in production and is well described in the prior art in many variations. The computer 15 will typically receive input signals from a variety of engine and environmental parameter sensors such as an exhaust gas oxygen sensor 16 in exhaust line 17, in order to generate the appropriate control signal for apparatus 11 to achieve clean and efficient combustion.

Different concentrations of alcohol and gasoline in the fuel mixture require different adjustments of the engine air-fuel ratio, thus computer 15 requires information regarding the proportion of alcohol to gasoline in the fuel mixture. The fuel composition sensor 20 measures the relative proportion of alcohol to gasoline in the fuel mixture being delivered to engine 10, and generates a fuel composition signal for use by computer 15. Any one of several such fuel composition sensors known in the art may be employed, but preferably, sensor 20 is a capacitive type for measuring the dielectric constant of the fuel flowing to engine 10.

As is well known, the dielectric constant of an alcohol-gasoline fuel mixture is directly related to the proportion of alcohol to gasoline in the mixture. Sensor 20 determines the dielectric constant of the fuel mixture passing through it, and generates an output capacitance signal. Analog-to-digital circuitry within computer 15 repeatedly reads the value of the capacitance signal, which is indicative of fuel composition, and stores the value in memory. A compensation factor for adjusting the engine air-fuel ration is then typically looked up in a permanent table in memory based upon the currently stored value of the capacitance signal.

The mechanical structure of dielectric sensor 20 is normally such that fuel flowing through it passes between and in contact with two separated electrodes that are coupled to a capacitance measuring circuit. A detailed description of the physical structure of a prior art capacitive sensor 20 and its associated capacitance measuring circuit as applied to air-fuel ratio control is provided in U.S. Pat. No. 4,915,084 issuing to E. V. Gonze on Apr. 10, 1990, which is hereby incorporated by reference into the present application.

One of the problems associated with alcohol-gasoline fuels, that has not previously been addressed in the prior art, is that of fuel contamination. It has been found that alcohol based fuels, especially those containing methanol, have the capacity to dissolve large quantities of water and other ionic contaminants due to the relatively large dipole moment associated with alcohols. In significant amounts, these dissolved fuel contaminants can cause premature failure of components in the fuel supply system due to their highly corrosive nature.

Consequently, there exists a need for a method and apparatus for detecting dissolved contaminants in an alcohol-gasoline fuel mixture and providing a warning indication when the fuel mixture is considered to be substandard in quality due to an unacceptable degree of contamination.

Figure 2:
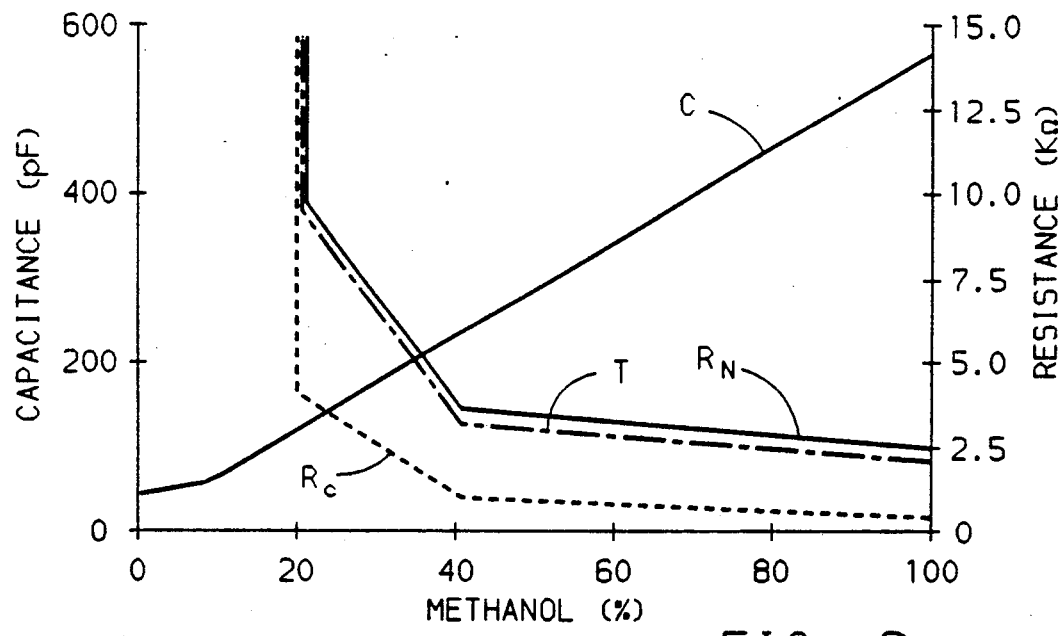
FIG. 2 graphically illustrates data obtained by measuring the resistance and capacitance appearing across two sensor electrodes of the fuel sensor shown in FIG. 1 for different methanol-gasoline mixtures flowing through it.

Referring now to FIG. 2, there is shown graphical representations of data obtained by measuring the electrical resistance and capacitance appearing across the sensing electrodes of the prior art sensor 20 described in the above U.S. Pat. No. 4,915,084 for different mixtures of an alcohol (in this case methanol) and gasoline flowing between the sensing electrodes. The resistance and capacitance data was measured by connecting a standard commercially available impedance meter across the sensor electrodes and then varying the composition of the fuel mixture flowing through the sensor.

As known by those skilled in the art, the measured capacitance of sensor 20, as represented by curve C in FIG. 2, increases in an approximately linear fashion as the percentage of methanol in the fuel mixture increases. This is due to the large difference between the dielectric constants of methanol and gasoline. Methanol has a relative dielectric constant in the order of 34.0 compared with approximately 2.0 for that of gasoline. In fact, the effective dielectric constant of the fuel mixture is equal to the measured capacitance multiplied by a constant, which is determined by the physical geometry of the sensing electrodes (i.e. size, spacing, and, shape).

Curves $R_N$ and $R_C$ of FIG. 2 represent respectively, the measured resistance appearing across the sensing electrodes of sensor 20 for uncontaminated (relatively pure) and highly contaminated mixtures of methanol and gasoline. The highly contaminated mixtures represent the severest degree of contamination that is expected to occur in practice. As will be understood by those skilled in the art, the fuel resistivity is equivalent to the measured sensor resistance multiplied by a constant, which is determined by the geometry of the sensing electrodes. Although the data presented in FIG. 2 is restricted to methanol-gasoline fuel mixtures, other alcohols such as ethanol behave similarly when mixed with gasoline and contaminated with water and other ionic contaminants.

Accordingly, the Applicants have recognized that the electrical resistivity of an alcohol-gasoline fuel mixture provides a good indication of the degree of contamination of the fuel mixture, and that an indication of substandard fuel quality can be made based upon this relationship. Broadly, this is accomplished by measuring the electrical resistivity of the alcohol-gasoline fuel mixture, which varies in accordance with the amount of dissolved contaminants; and providing an indication of substandard fuel quality when the measured resistivity of the fuel mixture is less than a threshold amount.

Figure 3:
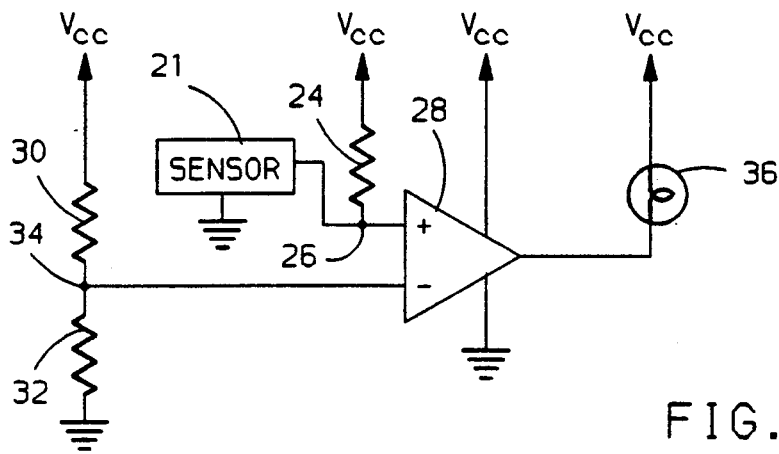
FIG. 3 illustrates an apparatus for detecting and indicating that an alcohol-gasoline fuel mixture is unacceptably contaminated based upon a measurement of fuel mixture resistivity.

Referring now to FIG. 3, an embodiment of the present invention for carrying out the above steps will now be described. Consider for the present that fuel resistivity sensor 21 has the same physical structure as the fuel composition sensor described in the above mentioned U.S. Pat. No. 4,915,084, and that it is inserted in the fuel supply line 13 of engine 10 in the manner indicated in FIG. 1. This being the case, the resistance appearing between the sensing electrodes of sensor 21 will vary as illustrated in FIG. 2 for different mixtures of methanol and gasoline delivered to engine 10.

A circuit for measuring the resistance of fuel sensor 21, and hence the resistivity of the fuel mixture, is formed by connecting a resistor 24 to sensor 21 at junction 26, and then connecting this series combination of the resistor 24 and sensor 21 between electrical ground and a fixed voltage potential $V_{cc}$, such as provided by a conventional regulated power supply (not shown). It will be understood by those skilled in the art that this fashion of connecting sensor 21 and resistor 24 forms a voltage divider, and the magnitude of the voltage potential appearing at junction 26 represents a resistance signal indicative of the resistance of sensor 21, and hence the resistivity of the alcohol-fuel mixture flowing through it.

The value of resistor 24 is set at approximately the midpoint of the desired range of resistance for sensor 21 that is to be measured. This tends to equalize the sensitivity of the resistance signal appearing at junction 26 for similar changes in sensor resistance over the range. For example, when sensor 21 has the physical structure described in U.S. Pat. No. 4,915,084, the sensor resistance will vary over the range from 0-10 K$\Omega$ for varying degrees of contaminated methanol-gasoline mixtures having methanol concentrations of at least 20%. For this range of sensor resistance, the value of resistor 24 can be set at 5 K$\Omega$.

Note that by selecting the value of resistor 24 in above fashion, the measurement of changes in sensor resistance for contaminated fuel mixtures having less than 20% methanol will be compromised. This has been found to be quite acceptable in practice, since the total quantity of contaminants that are dissolved in fuel mixtures having less than 20% methanol are considered relatively insignificant compared to amount of contaminants that can be dissolved in fuel mixtures having higher methanol concentrations. If for some reason it would be desirable to measure the resistivity of fuels mixtures having less that 20% methanol, the value of resistor 24 could be increased to improve the sensitivity of the resistance signal to the expected changes in sensor resistance for these fuel mixtures (approximately 4 K$\Omega$ to 250 K$\Omega$ for the present fuel sensor with fuels having less than 20% methanol).

In order to provide an indication of substandard fuel quality when the fuel mixture resistivity is less than a threshold amount, the resistance signal at junction 26 is coupled to the non-inverting input of a conventional operational amplifier 28, which is configured to operate as a comparator. For this type of operation, resistors 30 and 32 are connected in series to form a junction 34 between electrical ground and the voltage potential $V_{cc}$. Junction 34 is then connected to the inverting input of the operational amplifier 28. In this configuration, the operational amplifier 28 functions as a voltage comparator, i.e. the voltage of the resistance signal at the non-inverting input is compared with the voltage appearing at the inverting input. When the voltage of the resistance signal is greater than the voltage at the inverting input, the output of operational amplifier 28 is approximately held at the voltage potential $V_{cc}$. As a result, current flow through lamp 36 is prevented and lamp 36 will not be lighted. On the other hand, if the voltage of the resistance signal falls below the voltage at the negative input, the output of the operational amplifier 28 switches to ground potential, thereby allowing current to flow through and light lamp 36.

The threshold at which the output voltage of the operational amplifier switches so that lamp 36 can be lit to provide a warning indication is determined by the resistance values of resistors 30 and 32. When resistors 30 is selected to have the same value as resistor 24 (5 k$\Omega$ in the present embodiment), the value of resistor 32 then corresponds to a fixed threshold resistance for sensor 21 (or the related resistivity of the fuel mixture), below which lamp 36 will switch on to provide an indication of unacceptable fuel mixture contamination. For example, if resistor 32 is set to a value of 1.25 K$\Omega$, contaminants in the fuel mixture causing the resistance of sensor 21 to fall below this fixed resistive threshold will light lamp 36 to indicate unacceptable fuel contamination.

The apparatus illustrated in FIG. 3 provides a simple and practical embodiment for carrying out the present invention; however, by fixing a constant threshold amount (the value of resistor 32), the degree of fuel contamination required to produce an indication of substandard quality will vary depending upon the composition of the fuel mixture.

Figure 4:
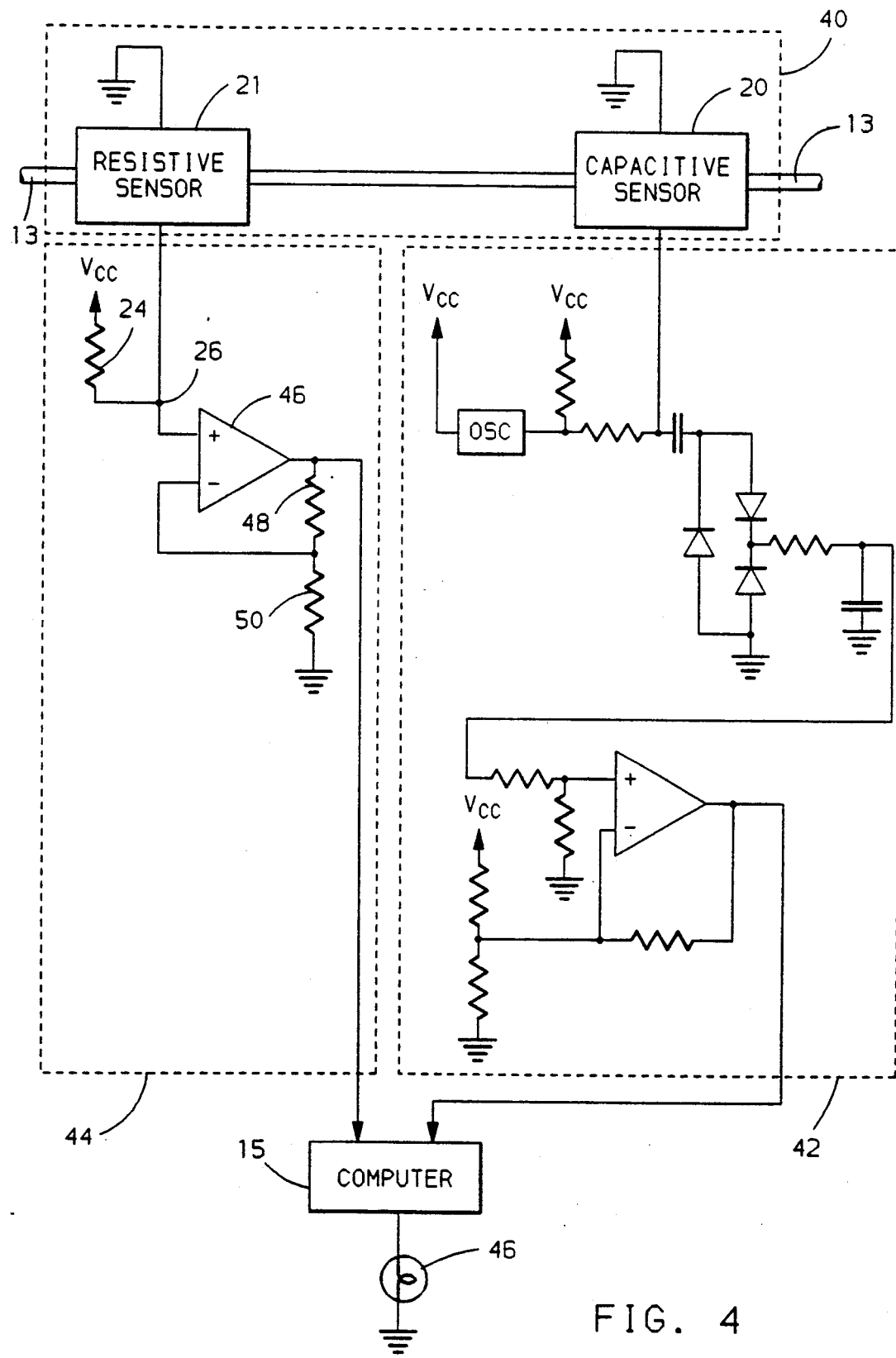
FIG. 4 illustrates an apparatus for detecting and indicating that an alcohol-gasoline fuel mixture is unacceptably contaminated based upon measurements of fuel mixture resistivity and dielectric constant.

Referring now to FIG. 4, there is shown a further embodiment of the present invention, which includes means for measuring the relative proportion of alcohol to gasoline in the fuel mixture and means for selecting the resistive threshold amount based upon the composition of the fuel mixture.

In this embodiment, a sensor means 40 is positioned in the engine fuel supply line 13. This sensor means 40 includes the prior art capacitive sensor 20 for measuring the fuel dielectric constant (conventionally used for engine air-fuel ratio control) and a resistive sensor 21 for measuring the resistivity of the fuel mixture.

Capacitive sensor 20 is coupled to a capacitance measuring circuit 42, which develops an output capacitance signal directed to computer 15. This output capacitance signal is indicative of the dielectric constant of the fuel mixture flowing through sensor 20, and hence the fuel composition (relative proportion of alcohol to gasoline). Preferably, sensor 20 and the capacitance measuring circuit 42 are identical in structure and function to the sensor and associated circuitry described in detail in the above mentioned U.S. Pat. No. 4,915,084, that has been previously incorporated by reference into the present application. Accordingly, prior art sensor 20 and its associated capacitance measuring circuitry are shown schematically in FIG. 4 without further discussion, in order to simplify the present description.

As stated previously, resistive sensor 21 is also considered to have the same physical structure as that of the prior art fuel sensor 20, although any known sensor configuration capable of measuring fuel resistivity could be used as an alternative. Resistive sensor 21 is coupled to a resistance measuring circuit 44, which includes a resistor 24 connected in series with sensor 21 across electrical ground and the fixed voltage potential $V_{cc}$, thereby forming a voltage divider as discussed in the description associated with FIG. 3. Again, the magnitude of the voltage that appears at junction 26, represents a resistance signal indicative of the sensor resistance, and hence fuel resistivity. In this embodiment, the resistance signal is directed to the non-inverting input of an operational amplifier 46 that is configured for amplifier operation. The output signal provided by the operational amplifier 46 represents an amplified version of the resistance signal, which is then provided as an input to computer 15. As will be recognized by those skilled in the art, the gain of the amplifier is fixed by the values of resistors 48 and 50, which are generally selected to maximize the voltage swing of the amplifier output signal, while ensuring compatibility with the input analog-to-digital conversion circuitry within computer 15.

A Lamp 46 is connected to a standard output driver within computer 15. The output driver can be set from an off to an on mode to supply current to light lamp 46 for indicating that fuel of a substandard quality is being delivered to the engine.

As stated previously, computer 15 is a conventional programmable engine control computer described in numerous variations in the prior art. Typically computer 15 includes the standard elements of a central processing unit, random access memory, read only memory, analog-to-digital and digital-to-analog converters, input/output circuitry, and clock circuitry. Generally, computer 15 is programmed to continuously execute a main looped engine control program, once the appropriate internal counters, timers, registers, and flags are initialized after engine start up.

Figure 5:
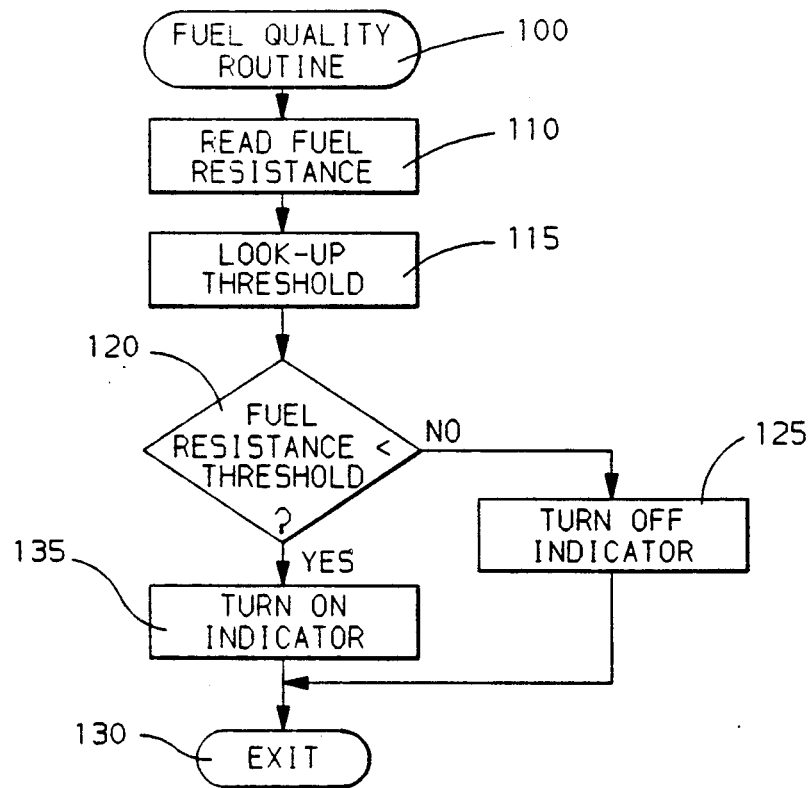
FIG. 5 shows a flow diagram representative of the steps executed by the computer shown in FIG. 4, when detecting and indicating that an alcohol-gasoline fuel mixture is unacceptably contaminated based upon measurements of fuel mixture resistivity and dielectric constant.

Shown in FIG. 5 is a flow diagram representative of the steps in a fuel quality routine stored in computer 15 and executed as part of the main looped engine control program, when operating in accordance with the principles of the present invention.

The fuel quality routine is entered at point 100, and immediately proceeds to step 110 where the value of the fuel resistance signal is read and stored in the memory of computer 15.

Next at step 115, a value for the threshold is looked up in a table stored in memory as a function of the current value of the fuel capacitance signal, which is indicative of the composition of the fuel mixture. Recall from the discussion associated with FIG. 1 that the fuel capacitance signal input to computer 15 is repeatedly read during engine operation for conventional air-fuel ratio control. Thus, the steps of reading and storing the value of the capacitance signal will occur elsewhere in the main looped engine control program, and the current value of the capacitance signal can be fetched from memory when needed for the table look up of the threshold value at this step. Look up table values for the threshold amount are selected to vary as a function of the fuel sensor capacitance (i.e., the percentage of alcohol in the fuel mixture), in a predetermined fashion, such as illustrated by the threshold curve T presented in FIG. 2.

After completing step 115, the routine passes to step 120 where a decision is required as to whether the value of the fuel resistance signal read at step 11 is less than the threshold amount looked up at step 115. If the value for fuel resistance signal is not less than the threshold amount, the fuel is judged not to be unacceptably contaminated and the routine passes to step 125. However, if the value for the fuel resistance is less than the threshold amount, the fuel is judged to be unacceptably contaminated and the routine proceeds instead to step 135.

When the routine proceeds to step 135, an output driver circuit within computer 15 is turned on to provide power to light the indicator lamp 46 connected to computer 15 (see FIG. 4). If the routine proceeds to step 125, the output driver will be set to the off mode (if not already in this mode) to ensure that the indicator lamp is not lit. From step 125 and step 135, the program passes to point 130, where the routine is exited.

It will be recognized that the above embodiment provides for a variable rather than a fixed threshold amount (as did the embodiment shown in FIG. 3). Consequently, an indication that the fuel mixture is of substandard quality is made based upon the degree of fuel contamination, independently of fuel mixture composition.

It will also be understood by those skilled in the art, that further steps can be included in the fuel quality routine of FIG. 5 to reduce false indications of unacceptable fuel quality induced by noise pickup or transients in the measurement circuitry. For example, steps could be added just prior to step 135 to assure that the measured fuel resistance is less than the threshold for at least two (or even more) consecutive passes through the routine before turning on the driver to light the indicator lamp 46 at step 135.

In both of the embodiments illustrated in FIGS. 3 and 4, the resistive fuel sensor 21 was described as having the same physical structure of the prior art capacitive sensor disclosed in U.S. Pat. No. 4,915,084. This was done primarily to facilitate and simplify the description and should be considered as merely exemplary. The fuel sensor 21 may in fact have any of a number of possible physical configurations. The only requirement being that sensing electrodes are needed for measuring the resistivity of the fuel mixture flowing through the sensor.

Figure 6:
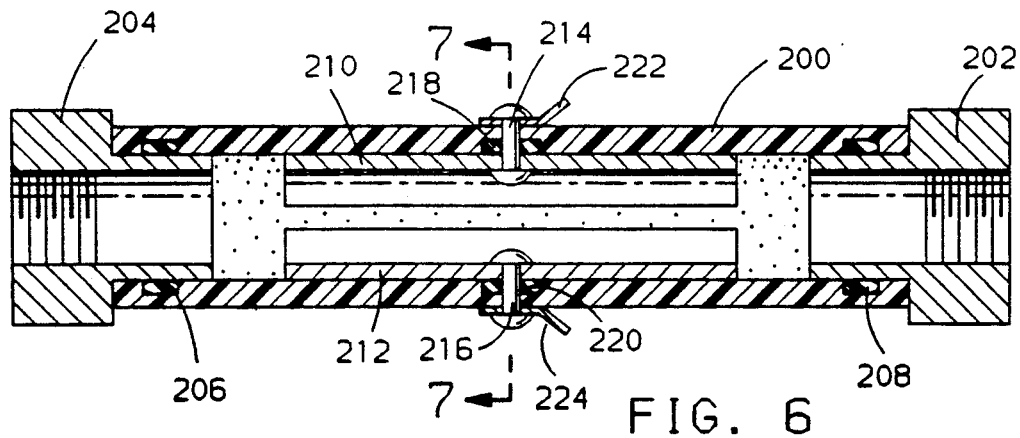
FIG. 6 shows a cutaway view of an alternative sensor for measuring the resistivity of an alcohol-gasoline; fuel mixture.
Figure 7:
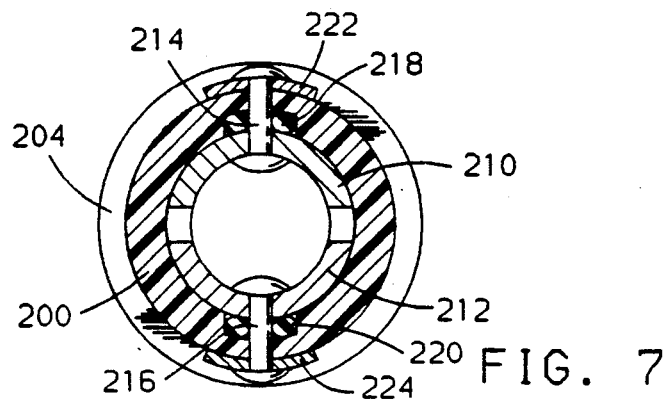
FIG. 7 shows a sectional view of the fuel sensor shown in FIG. 6 along the line 7—7.

Referring now to FIGS. 6 and 7, there are shown respectively, a cutaway view of an alternative resistive fuel sensor and a sectional view of the alternative sensor along the line 7—7 of FIG. 6. A cylindrical casing 200 is formed of an electrically non-conducting material such as nylon, which is resistant to alcohol-gasoline fuel mixtures. Stainless steel fuel line fittings 202 and 204 are inserted into the open ends of casing 200. O-rings 206 and 208 are employed to preventing the leakage of fuel between the casing 200 and the inserted fuel line fittings 202 and 204. Two stainless steel electrodes 210 and 212 are spaced apart inside the cylindrical casing 200, and are held in position by electrically conducting rivets 214 and 216, which respectively pass through electrodes 210 and 212 and the walls of casing 200 as illustrated. Terminals 222 and 224 are fixed between the casing 200 and the flattened ends of rivets 214 and 216 to provide a means for making electrical connection to the internal sensing electrodes 210 and 212. O-rings 218 and 220 surrounding rivets 214 and 216 prevent fuel from leaking between the casing and rivets.

The resistance appearing across the terminals 222 and 224 of the alternative sensor configuration will be representative of the resistivity of fuel flowing through casing 200. Since the physical structure of the alternative fuel sensor differs from that of prior art sensor 20 described in U.S. Pat. No. 4,915,084, it will be understood that different resistor values will generally be required when using this or other alternative sensors with the resistive measuring circuits shown in FIGS. 3 and 4.

Figure 8:
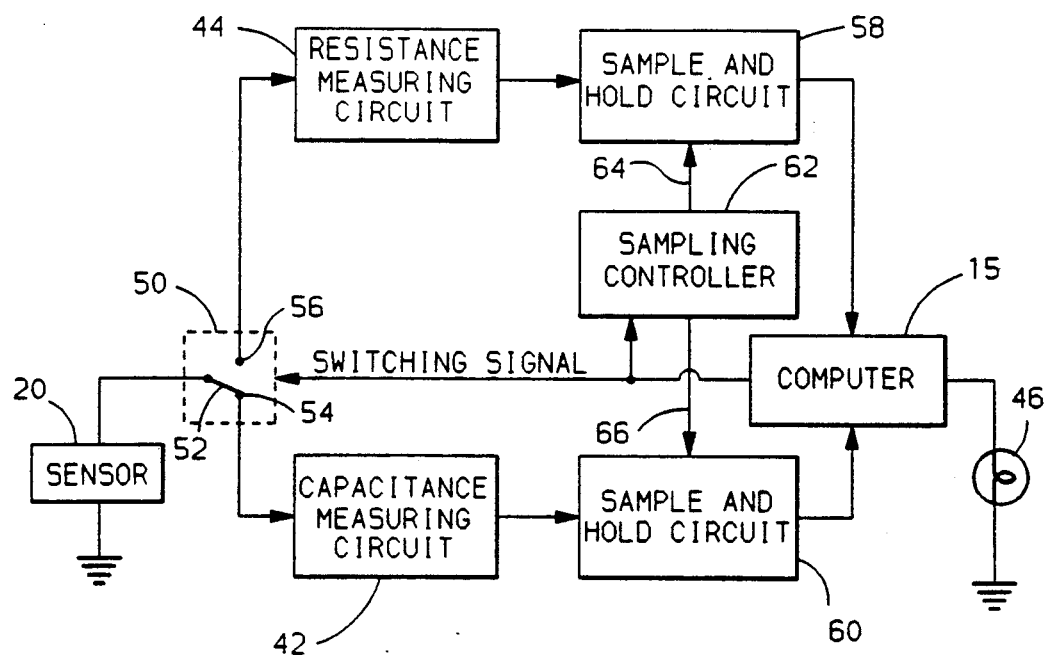
FIG. 8 illustrates an apparatus for detecting and indicating that an alcohol-gasoline fuel mixture is unacceptably contaminated, by alternately switching a single fuel sensor between circuitry employed for measuring the fuel dielectric constant and the fuel resistivity.

A final embodiment of the invention is shown in block diagram form in FIG. 8. A single fuel sensor 20 is switched between previously described capacitance measuring circuit 42 and resistance measuring circuit 44 (see the discussion related to FIG. 4) by means of a commercially available solid state switch 50. Switch 50 is shown diagrammatically as having one terminal 56 connected to the input of resistance measuring circuit 44 and another terminal 54 connected to the input of capacitance measuring circuit 42. Sensor 20 is connected to switchable terminal 52, which for the present description can be considered to normally be connected to terminal 54, but shifts to connect with terminal 56, when the appropriate SWITCHING SIGNAL is provided by computer 15.

Since sensor 20 is alternately switched between the inputs of the resistance and capacitance measuring circuits 42 and 44, each measuring circuit will generate an erroneous output signal during the time period that the sensor is connected to the other measuring circuit. To avoid false resistance and capacitance signals from being directed as input to computer 15, conventional sample and hold circuits 58 and 60 are interposed between the measuring circuits and computer 15.

The sample and hold circuits 58 and 60 operate in conjunction with sampling controller 62, which provides sampling control signals via leads 64 and 66.

When either of the sample and hold circuits 58 or 60 receives a pulsed control signal from the sampling controller 62, the signal at the input of the sample and hold circuit is sampled and then held, until the next pulsed control signal is received from the sampling controller 62.

The sampling controller 62 includes standard clock circuitry for generating a repetitively pulsed control signal. This pulses control signal is gated to one or the other of the sample and hold circuits 58 and 60, depending upon the state of the SWITCHING SIGNAL. When the state of the SWITCHING SIGNAL is such that the sensor 20 is connected to the capacitive measuring circuit 42, the pulsed control signal generated within the sampling controller 62 is gated to activate the sample and hold circuit 60 associated with the capacitance measuring circuit. Likewise, when the sensor 20 is switched to connect with the resistance measuring circuit 44 via the SWITCHING SIGNAL, the pulsed control signal generated by the sampling controller 62 is then gated to activate the sample and hold circuit 58 associated with the resistance measuring circuit 44.

Those skilled in the art will recognize that the gating of the pulsed control signal within sampling controller 62 can be easily implemented using standard electronic logic circuits. For example, if the solid state relay 50 connects sensor 20 to contact 54 when the SWITCHING SIGNAL is in its low state, then the appropriate gated control signal for lead 66 can be obtained at the output of a standard AND gate having the clock generated pulsed control signal and the inverted SWITCHING SIGNAL as inputs. This being the case, the gated control signal for lead 64 can be obtained at the output of a standard AND gate having as inputs, the clock generated control signal and the SWITCHING SIGNAL (which would be at its high state to connect sensor 20 to terminal 56).

As with the previous embodiment, an indication of substandard fuel quality or unacceptable contamination is provided by lighting lamp 46, which is connected to a driver circuit within computer 15.

Figure 9:
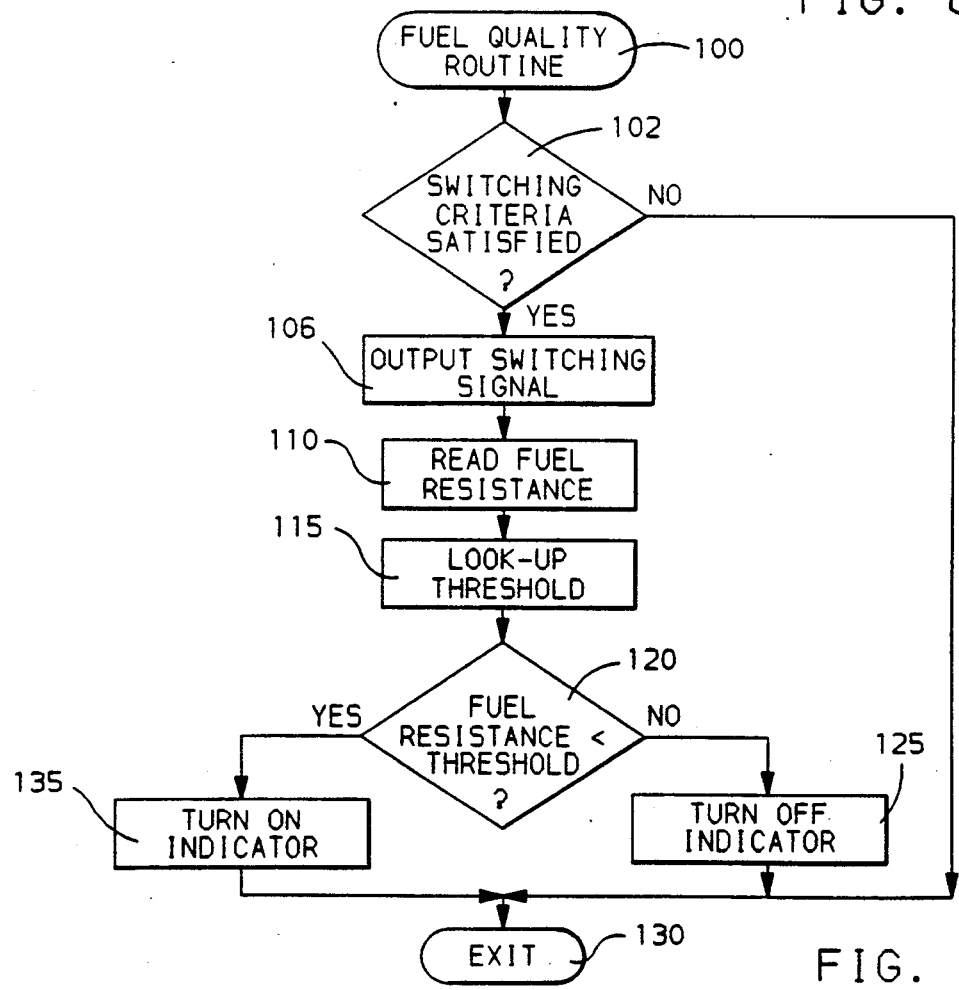
FIG. 9 shows a flow diagram representative of the steps executed by the computer in FIG. 8, when switching the fuel sensor between the measurement circuitry employed for detecting and indicating that an alcohol-gasoline fuel mixture is unacceptably contaminated.

Referring now to FIG. 9, there is shown a flow diagram representative of the program step executed by the computer 15, in carrying out the invention for the embodiment illustrated in FIG. 8).

After entering the routine at point 100, a decision is required at step 102 as to whether predetermined switching criteria is satisfied. If the switching criteria has not been satisfied, the routine is exited at point 130. However, when the switching criteria is satisfied, the routine passes to step 106.

As used in the present specification and accompanying claims, the term switching criteria refers to a predetermined condition or conditions under which sensor 20 is to be switched from the capacitive measuring circuitry 42 to the resistive measuring circuit 44. Sensor 20 is normally connected to the capacitive measuring circuit 42, which is consistent with the conventional usage of sensor 20 for accurate air-fuel ratio control. This switching of the sensor 20 from the capacitive measuring circuit 42 to the resistive measuring circuit 44 does not have to occur with great frequency, since a change in fuel resistivity will normally occur only after additional fuel is added to the engine fuel tank 12.

The switching criteria can be satisfied by the occurrence of any of number of conditions that are customarily sensed by computer 15, such as (1) the laps of a predetermined time after the engine is started, as established by a counter internal to computer 15; (2) at a time immediately after the engine ignition is switched off, during the short period that computer 15 typically remains activated; or (3), at predetermined time intervals as the engine is operated, in accordance with a timer internal to computer 15.

When the switching criteria is satisfied at step 102, the program proceeds to step 106, where computer 15 outputs the appropriate SWITCHING SIGNAL to solid state switch 50 and the sampling controller 62, so that sensor 20 is switched to connect with the input of the resistance measuring circuit 44 and the resulting value of the output resistance signal is sampled and held by the sample and hold circuit 58. Consistent with the previous discussion, the SWITCHING SIGNAL is pulsed to shift from its low state to its high state just long enough to sample and hold an accurate value for the fuel resistance signal provided by resistance measuring circuit 44.

The remainder of the steps in the routine are identical to the steps carried out in the routine presented in FIG. 5. Consequently, the previous description associated with these steps will not be repeated in the present discussion.

The switching circuitry and associated control for the present embodiment provides the advantage that a single sensor can be used to measure both fuel dielectric constant and resistivity. This reduces the both expense and complexity of the sensing means required for sensing the electrical properties of the alcohol-gasoline fuel mixtures. In addition, it has been found that the corrosive effect of the fuel on the sensor electrodes is diminished, since the period of time that direct current is applied to the electrodes for measuring fuel resistivity is reduced by switching action.

In the above described embodiments, a fuel mixture containing methanol and gasoline was used for the purpose of explaining the principles and operation of the present invention. Other alcohols such as ethanol act similarly when mixed with gasoline and contaminated with water and other ionic components. Accordingly, it will be understood that use of methanol-gasoline fuel mixtures was exemplary and the present invention is equally applicable to alcohol-gasoline fuels in general.

Thus, the aforementioned description of the preferred embodiments of the invention is for the purpose of illustrating the invention, and is not to be considered as limiting or restricting the invention, since many modifications may be made by the exercise of skill in the art without departing from the scope of the invention.

The embodiments of the invention in which an exclusive property or privilege is claimed are defined as follows:

1. For an internal combustion engine having a fuel supply line through which a fuel mixture containing alcohol and gasoline is delivered to the engine, the fuel mixture having electrical properties characterized by an electrical resistivity and a dielectric constant, an apparatus for detecting and indicating that the fuel mixture is of a substandard quality due to an unacceptable amount of contaminants dissolved in the fuel mixture, the apparatus comprising:

a single sensor for sensing both the electrical resistivity and dielectric constant of the alcohol and gasoline fuel mixture being delivered to the engine;

resistance measuring means switchably coupled to the sensor means for developing a resistance signal indicative of electrical resistivity of the fuel mixture;

capacitance measuring means switchably coupled to the sensor means for developing a capacitance signal indicative of the dielectric constant of the fuel mixture;

means for alternatively switching the sensor between the resistance measuring means and the capacitance measuring means in accordance with predetermined switching criteria;

means responsive to the capacitance signal for selecting a threshold amount based upon the dielectric constant of the fuel mixture; and means responsive to the fuel resistance signal for providing an indication of substandard fuel quality when the resistivity of the fuel mixture is less than the threshold amount.

* * * * *